US012303428B2

(12) United States Patent
Decock et al.

(10) Patent No.: US 12,303,428 B2
(45) Date of Patent: May 20, 2025

(54) DEVICE FOR ASSISTING WITH THE USE OF A DEVICE FOR DISPENSING A LIQUID PRODUCT

(71) Applicant: Nemera La Verpillière, La Verpilliere (FR)

(72) Inventors: Thierry Decock, Lyons (FR); Guillaume Cerqueira, Lyons (FR); Gaëtan Painchaud, Francheville (FR)

(73) Assignee: NEMERA LA VERPILLIÈRE, La Verpilliere (FR)

( * ) Notice: Subject to any disclaimer, the term of this patent is extended or adjusted under 35 U.S.C. 154(b) by 128 days.

(21) Appl. No.: 17/436,851

(22) PCT Filed: Mar. 4, 2020

(86) PCT No.: PCT/EP2020/055753
§ 371 (c)(1),
(2) Date: Sep. 7, 2021

(87) PCT Pub. No.: WO2020/178358
PCT Pub. Date: Sep. 10, 2020

(65) Prior Publication Data
US 2022/0175579 A1    Jun. 9, 2022

(30) Foreign Application Priority Data

Mar. 5, 2019  (FR) ...................................... 1902248

(51) Int. Cl.
*A61F 9/00*        (2006.01)
(52) U.S. Cl.
CPC ................ *A61F 9/0026* (2013.01)

(58) Field of Classification Search
CPC .... A61F 9/0026; A61F 9/0008; A61M 35/003
See application file for complete search history.

(56) References Cited

U.S. PATENT DOCUMENTS 3,409,009 A * 11/1968 Vasse ................... A61F 9/0008
222/548
4,960,407 A * 10/1990 Cope ................... A61F 9/0026
604/300

(Continued)

FOREIGN PATENT DOCUMENTS

CN         1379651 A  * 11/2002   ........... A61F 9/0008
CN      204134034 U     2/2015

(Continued)

*Primary Examiner* — Ariana Zimbouski
(74) *Attorney, Agent, or Firm* — Farber LLC; Jonathan A. Winter (57) ABSTRACT

The invention relates to a device for dispensing a solution, having a body, the outer surface of which is intended to be held in at least one of a user's hands, and having at least one activation zone that is able to be acted upon by the user to cause the solution to be dispensed, and a head carried by the body, the head being provided with a contact surface for pressing on an area of a patient's body, the contact surface forming an outer contour, and with at least one orifice for dispensing the solution, the head being coupled to the body by connecting means that allow it to rotate with respect to the body about an axis of rotation substantially parallel to an axis of the body in order to modify the position of the contact surface with respect to the at least one activation zone.

15 Claims, 3 Drawing Sheets

(56) References Cited

U.S. PATENT DOCUMENTS

| | | | | |
|---|---|---|---|---|
| 5,058,778 | A | * | 10/1991 | Weinstein .............. B65D 83/00 |
| | | | | 222/548 |
| 9,072,581 | B1 | | 7/2015 | Alam et al. |
| 11,234,863 | B2 | * | 1/2022 | Lim et al. ............. A61F 9/0026 |
| 2005/0201811 | A1 | | 9/2005 | Russell et al. |
| 2006/0108378 | A1 | * | 5/2006 | Cohen .................. A61F 9/0008 |
| | | | | 222/211 |
| 2014/0151457 | A1 | * | 6/2014 | Wilkerson ........... H10N 30/802 |
| | | | | 73/579 |
| 2018/0177957 | A1 | | 6/2018 | Streeter et al. |
| 2018/0332895 | A1 | * | 11/2018 | Li ....................... A61M 11/042 |

FOREIGN PATENT DOCUMENTS

| | | |
|---|---|---|
| CN | 107096122 A | 8/2017 |
| CN | 109331332 A | 2/2019 |
| DE | 102011009504 A1 | 8/2011 |
| JP | 2018094420 A | 6/2018 |

\* cited by examiner

DEVICE FOR ASSISTING WITH THE USE OF A DEVICE FOR DISPENSING A LIQUID PRODUCT

FIELD OF THE INVENTION

The invention relates to a device for dispensing a solution on a part of a patient's body. It relates in particular to a liquid product to be dispensed in an organ, for example an eye or an area of the skin, which will be called the dispensing area. The patient may be a human or an animal.

BACKGROUND OF THE INVENTION

Devices for dispensing liquid products are already known in the state of the art. Document JP2018094420 describes an assistance device for assisting in the use of a device for dispensing an ophthalmic solution, comprising a gripping part, provided with concave gripping areas for holding between the user's fingers, in order to activate the dispensing of ophthalmic solution. The device further comprises a part for pressing on the user's face, around the eye. The purpose of this device is to make the dispensing of ophthalmic solution more comfortable for a user of the device. The situation can nevertheless be improved.

SUMMARY OF THE INVENTION

The invention aims in particular to provide a device for dispensing a solution, making the dispensing more comfortable for the user.

The invention therefore proposes a dispensing device for dispensing a solution comprising:
  a body, the outer surface of which is intended to be held in at least one of a users hands, and comprises at least one activation zone that is able to be acted upon by the user to cause the solution to be dispensed, and
  a head carried by the body, the head being provided with a contact surface for pressing on an area of a patient's body, the contact surface forming an outer contour, and with at least one orifice for dispensing the solution, the dispensing device being arranged so that the head is coupled to the body by connecting means that allow it to rotate with respect to the body about an axis of rotation substantially parallel to an axis of the body in order to modify the position of the contact surface with respect to the at least one activation zone.

Thanks to the connection that allows the head to rotate with respect to the body, it is possible to modify the orientation of the head, with respect to the body of the dispensing device used for gripping it, and therefore of the contact surface with respect to the activation zone located on the body. Consequently, when the head must take a specific position, for example if it has a shape complementary to that of a contour of one of the patient's eyes in order to be correctly seated, the body can be oriented with respect to the head so that it is easier for the user to grip and/or easier to activate the dispensing of the solution. For example, the user can use either the left hand or the right hand to handle the body and/or activate the dispensing of the solution. This improves the ergonomics of a device for dispensing a solution on an area of the patient's body, provides greater comfort for the user and better precision for the dispensing of the solution, and provides better adaptation to the specific morphology of each patient and/or user of the dispensing device. The user holding the body of the dispensing device can be the patient to whom the solution will be dispensed or a third party user assisting this patient, such as a member of the medical staff.

Another advantage is that the user can orient the body once the head is positioned on the area of the patient's body, thus avoiding an inadvertent displacement of the contact surface with respect to the area of the patient's body (and more precisely with respect to the dispensing area) when dispensing the solution.

This possibility of orienting the body with respect to the head, and therefore with respect to the contact surface, is especially interesting when the at least one activation zone has a restricted surface, arranged according to only an angular sector of the peripheral surface (i.e. when the at least one activation zone has a shape different from a shape of revolution, which means that the user must place his/her fingers at a predetermined position on the body). "An activation zone arranged on the peripheral surface and delimiting an angular sector" means an activation zone which is not arranged continuously on a contour of the peripheral zone. In other words, the peripheral surface comprises at least a contour comprising the at least one activation zone and an "inert" zone, adjacent to the at least one activation zone. Thus, the at least one activation zone has a shape different from a zone of revolution, which makes the proposed dispensing device even more ergonomic and intuitive for activation of the dispensing of the solution by the user.

According to other optional features of the dispensing device taken alone or in combination:
  The head of the dispensing device has a contour whose shape is different from a shape of revolution, for example a contour of oval or oblong cross-section. The term "shape of revolution" designates a shape that does not vary when it rotates about a fixed axis referred to as "axis of revolution" and of which any intersection with a plane perpendicular to the axis of revolution defines a circle. This allows a better adaptability to the patient's physiology and more comfort for using the dispensing device, especially if the dispensing zone is located around one of the patient's eyes.
  The body has a contour whose shape is different from a shape of revolution, for example a contour of oval cross-section. In this case, it is particularly interesting to be able to modify the orientation of the body with respect to the head, since the user holds the body by placing his/her fingers on each side of the diameter along the oval part (to press the device more easily), and it is more comfortable that the orientation of this diameter along the body be not imposed by the position of the head.
  The connecting means are adapted to make a connection of a type chosen from the group comprising at least: a pivot connection, a ball joint connection, a sliding pivot connection. Advantageously, the connecting means are configured to guide the rotation of the dispensing device body about the axis of the dispensing device body and to fix the dispensing device body to its head in the axial direction. In addition, a guiding element comprises for example an annular or semi-annular rib, or one or more guiding pins. Preferably, the rotation obtained between the body and the head comprises a pivot connection along an orientation axis substantially parallel to the axis of the body. In addition, the axis of the body preferably corresponds to a central axis of the body.

The connecting means comprise stopper elements adapted to limit the relative rotation of the body of the dispensing device with respect to its head. The angular displacement between the body and the head can therefore be limited. This will limit, for example, the risks of damaging the dispensing device by tearing, by making sure that the head does not project too much out from the body depending on the orientation and/or the rotation chosen by the user. Preferably, the stopper elements are configured to allow a maximum displacement angle of between 0° and 90°, preferably of between 0° and 45°.

The head and the body can take a relative position called storage position and the connecting means comprise means for returning the head to the storage position. In this storage position, the contours of the body and of the head can be aligned with each other when they are similar. This makes the device more compact and therefore limits the risks of the head being torn off during the packaging step, especially for storage.

The head is removably mounted with respect to the body. Various interchangeable heads can therefore be adapted on the body to increase the lifetime of the dispensing device, or to better adapt to the morphology of a patient depending on the area of the patient's body where the solution is to be dispensed using the dispensing device.

The connecting means comprise means for defining at least one predetermined position, for example a positioning notch, or friction means.

The head comprises means for detecting dispensed solution, preferably optoelectronic means.

The dispensing device comprises an electrical connection interface between the body and the head, comprising at least one conducting element, preferably an annular conducting element cooperating by physical contact with an additional conducting element.

The body is configured to receive two contact parts of different shape. For example and advantageously, the head is made from a thermoformable material and the body from another material.

BRIEF DESCRIPTION OF THE DRAWINGS

The invention will be better understood on reading the following description, given solely by way of example and with reference to the accompanying drawings in which.

DETAILED DESCRIPTION OF THE INVENTION

Figure 1:
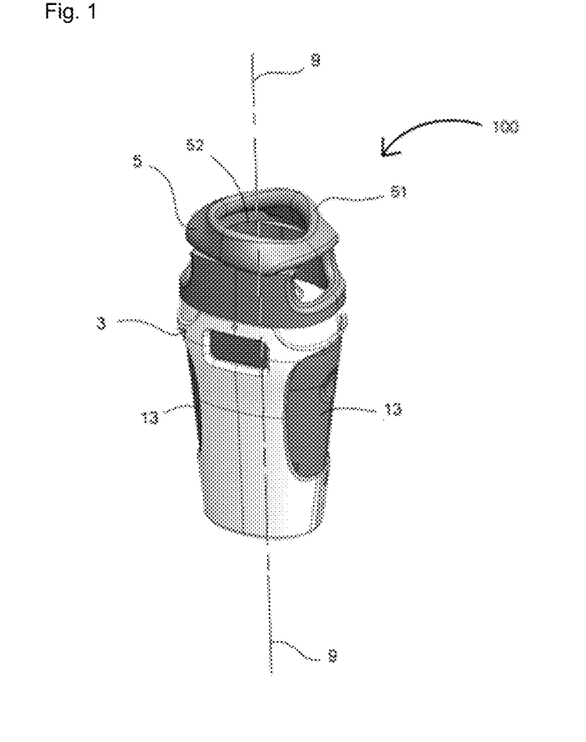
FIG. 1 is a perspective view of a dispensing device according to a first embodiment of the invention.

FIG. 1 illustrates a dispensing device 100 according to a first special and non-limiting embodiment of the invention.

The dispensing device 100 comprises a body 3 and a head 5. The shape of the dispensing device 100 is such that a cross-section of its body 3 is globally oval or oblong, in other words the shape of the body is different from a shape of revolution. The global shape of the head 5 also has an oval or oblong cross-section, in other words the shape of the head 5 is different from a shape of revolution. The outer surface 7 of the body 3 of the dispensing device 100 is intended to be held in at least one of a user's hands to dispense a solution contained in the dispensing device 100. The user holding the body 3 of the dispensing device 100 can be the patient to whom the solution will be dispensed or a third party user assisting this patient, such as a member of the medical staff.

Optionally, the body 3 comprises display means 11 useful to monitor the dispensing of the solution contained in the dispensing device 100.

The outer surface 7 of the body 3 of the dispensing device 100 comprises at least one activation zone 13 that is able to be acted upon by the user to cause the solution contained in the dispensing device 100 to be dispensed. According to a preferred embodiment of the invention, two activation zones 13 comprise each a mechanical element configured to compress a tank inside the body 3 of the dispensing device 100 in order to dispense a solution contained in the tank. These mechanical elements are returned by return means to a position corresponding to absence of dispensing. The return means can be provided by elasticity of the tank or by added elements such as springs.

The head 5 of the dispensing device 100 is carried by the body 3. The head 5 is provided with a contact surface 51 for pressing on an area of the body of a patient to whom the solution is dispensed. The head 5 also comprises an orifice 52 (or opening) for dispensing the solution to an area of the body of the patient to whom the solution is dispensed. Depending on the configuration of the head 5, the contact surface 51 may form a contour of the orifice 52, for example when the dispensing device 100 is configured to dispense an ophthalmic product. Advantageously, the shape of the contour can be different from a shape of revolution, for example an oval shape, to make the dispensing of an ophthalmic solution in drop form more comfortable. According to other variants, the contact surface can be flat and comprise one or more orifices, to dispense a solution over an area of the patient's skin. According to another variant, the head may take the shape of a nozzle whose shape is adapted for a nasal application or oral dispensing. The head may also have a concave shape delimited by a projecting contour, the concave part being provided with one or more orifices to dispense the solution contained in the dispensing device 100 over an area of the patient's body delimited by pressing the projecting contour on the skin. Obviously, these examples are not limiting.

Advantageously, the head 5 of the dispensing device 100 is coupled to the body 3 by connecting means that allow it to rotate with respect to the body 3 in order to modify the position of the contact surface 51 with respect to the at least one activation zone 13.

According to the preferred embodiment of the invention shown on FIG. 1, the head 5 is coupled to the body 3 of the dispensing device 100 by a pivot connection that allows the head 5 to rotate about an axis of rotation 9 substantially parallel to the axis of the body 3. In addition, the axis of the body 3 preferably corresponds to a central axis of the body 3.

According to variants of the invention, the connecting means are configured to allow a sliding pivot connection of the head 5 with respect to the body 3 or form a ball joint connection between the body 3 and the head 5.

The dispensing device 100 is configured to be able to contain and dispense a solution in the form of a liquid, gel or foam.

The dispensing device 100 is further adapted to dispense a solution, depending on its form, for direct application over an area of the patient's body, or a spray, or in the form of a mist when the solution is liquid.

Thus, the dispensing device 100 can be adapted to various applications such as the dispensing of medicine or paramedical products, the dispensing of cleaning products such as collyrium drops, for example, or in the veterinary field, these examples not being limiting.

Rotation of the head 5 of the dispensing device 100 with respect to its body 3 is especially interesting when the activation zone 13 has a restricted surface or at least is arranged according to only an angular sector of the outer surface of the body 3. In other words, this means that the activation zone 13 has a shape different from a shape of revolution and that the user cannot place his/her hand or fingers in an undetermined position to hold the body 3 when the activation zone 13 has a restricted size with respect to the total outer area 7 of the body or if activation of the dispensing requires an intervention over several activation zones 13 at the same time. This is the case, for example, if the body 3 has two activation zones 13 arranged on each side and diametrically opposed with respect to the axis of rotation 9, as shown on FIG. 1.

FIG. 1 shows a body 3 comprising two activation zones 13, each having a shape different from a shape of revolution. The user of the dispensing device 100 must therefore hold the body 3 according to a predetermined position of his/her fingers, in particular when the activation zones 13 have a restricted size with respect to the total outer area of the body 3.

Figure 2:
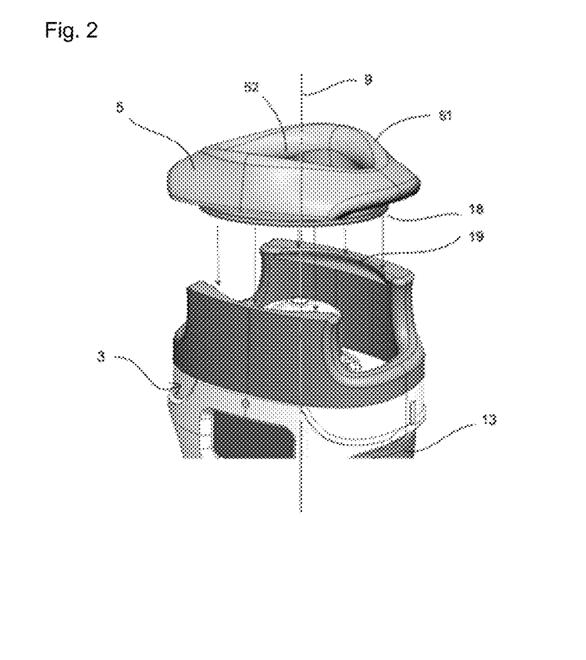
FIG. 2 is an exploded perspective view of a part of the dispensing device shown on FIG. 1.

According to the embodiment shown on FIG. 1, the connecting means between the body 3 and the head 5 are adapted so that the head 5 can rotate with respect to the body 3 by inserting the head 5 on a first annular surface of the body 3 comprising at least one rib 19 (shown on FIG. 2). Thus, a groove 18 (shown on FIG. 2) arranged on a second annular surface of the head 5 is combined with the rib 19 arranged on the first annular surface of the body 3, after assembly. Similarly, the groove 18 can be arranged on the body 3, the rib 19 then being arranged on the head 5. According to a variant, several grooves and ribs are combined to form the connecting means between the body 3 and the head 5. According to this embodiment, the connection thus obtained prevents translation of the head 5 with respect to the body 3 but allows complete rotation of the head 5 about the axis of rotation 9.

Artfully, the annular surfaces of the body 3 consist of arcs of a circle diametrically opposed with respect to the axis of rotation 9, so that the head 5 and the body 3 can be coupled together without having to apply too much force, possibly benefiting from the elasticity of the materials used to manufacture the body 3 and/or the head 5 in the connecting area. The head 5 and the body 3 are therefore connected together by "clipping" (or snap-fastening).

Thus, the head 5 can advantageously be removably mounted with respect to the body 3, which offers the advantage of being able to replace the head 5 and increase the lifetime of the dispensing device 100 or of being able to use several heads, for example each one being adapted to a particular use or to a morphology of the patient to whom the solution will be dispensed.

For example, the head 5 can be chosen according to the dimension of an element specific to the patient's physiognomy, according to his/her size, shape or fragile nature. These examples are not limiting.

For example, it is possible to use a head 5 whose contour has a contact surface 51 of small dimensions to dispense an ophthalmic product or a cleaning product to an infant or a young child, while a head with a larger contour will be preferred to dispense the same type of product to an adult.

FIG. 2 is an exploded perspective view of the top part of the dispensing device 100 shown on FIG. 1, illustrating the connecting means 18, 19 used to realize a rotating connection of the head 5 with respect to the body 3 about the axis of rotation 9 of the dispensing device 100.

Depending on the configuration of the dispensing device 100, the axis of rotation 9 may correspond to a dispensing axis for dispensing the solution contained in the dispensing device 100. A "dispensing axis" means an axis defined by the direction of displacement imposed on the solution when dispensing through the dispensing orifice(s) arranged in the body 3.

Advantageously, the connecting means 18, 19 comprise means for defining at least one predetermined position, for example a positioning notch, or friction means. The rotation of the head 5 with respect to the body 3 can therefore be limited so that the parts of the head 5 do not project too much with respect to the assembly of the dispensing device 100 and/or so that in this configuration, there is no risk of accidentally tearing off the head 5. This is especially the case when the cross-section of the assembly of the dispensing device 100 is globally oval or oblong, allowing in particular better gripping or ergonomics adapted to activation via the two activation zones 13, using for example two of the user's fingers.

According to one embodiment of the invention, the dispensing device 100 comprises means for returning the head 5 to a storage position with respect to the body 3. Thus, if the head 5 is returned to the storage position and if in this storage position, the assembly of the dispensing device 100 has a profile adapted for being inserted into a packaging element such as a box or a case, it is easier to store the dispensing device 100 in the packaging element.

The return means may comprise two points for attaching a spring used in traction or compression with, coupled to the spring, a first attachment point arranged on the body 3 and a second attachment point arranged on the head 5. According to a variant, the spring effect can be produced by combining a lug moving along a flexible tab of increasing thickness as the head 5 moves with respect to the body 3 so that the flexible tab acts as a compression spring. According to this configuration, the tab can be securely attached to the body 3 and the lug pressing on the tab can be securely attached to the head 5, or vice versa. These examples are not limiting.

According to one embodiment of the invention, the means for connecting the head 5 to the body 3 include at least one element for guiding the head 5 in translation with respect to the body 3, in addition to the ability to provide a pivot connection. For example, a trunk supporting connecting elements as mentioned above for connecting the body 3 carries these connecting elements mounted on a cylinder sliding in a tube arranged in the body using a sealed connection, the trunk being mounted on a compression spring to create a damping effect when the contact surface 51 of the head 5 comes into contact with an area of the body of the patient to whom the solution will be dispensed. Thus, contact with fragile areas of the patient's body is improved and user comfort is increased. This is particularly advantageous when dispensing an ophthalmic solution in one of the patient's eyes.

Figure 3:
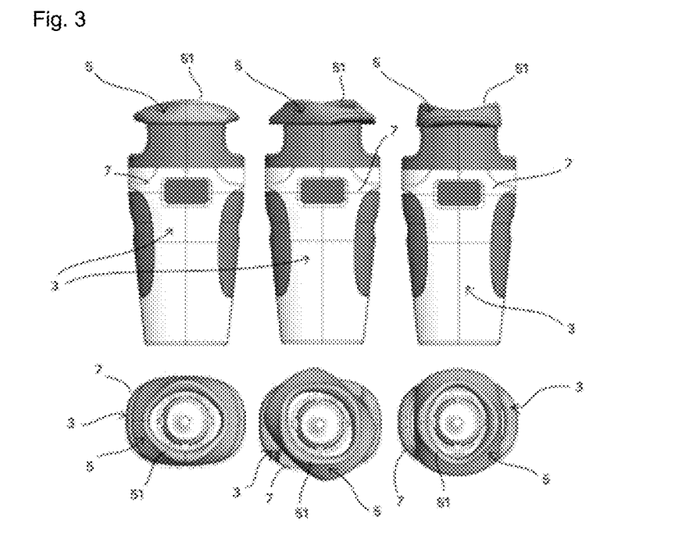
FIG. 3 comprises front and top views of the dispensing device already shown on FIGS. 1 and 2, illustrating different positions of the head of the dispensing device with respect to the body of the dispensing device.

FIG. 3 illustrates various positions of the head 5 of the dispensing device 100 with respect to its body 3. The top part of the figure shows three front views of the dispensing device 100 corresponding respectively to three relative positions of the head 5 with respect to the body 3 of the dispensing device 100. The bottom part of the figure shows three top views of the dispensing device 100 corresponding to the front views shown in the top part.

Thus, the front and top views shown on the left of FIG. 3 represent the dispensing device 100 when the head 5 is oriented in a nominal position, also referred to as the storage position. In this storage position, the head 5 has a zero angle of rotation with respect to the body 3.

The front and top figures, shown in the center of FIG. 3, represent the dispensing device 100 when the head 5 has been oriented by a rotation through an angle of 45 degrees clockwise with respect to the body 3, and with respect to the storage position shown on the left of the same figure. Advantageously, this improves the ergonomics and increases the comfort when the user applies the contact surface 51 of the head 5 on an area of a patient's body, for example the contour of an eye, and activates dispensing immediately afterwards by manually pressing on the activation zone(s) 13, in particular when the activation zone 13 is defined according to an angular sector on the outer surface 7 of the body 3.

The front and top figures, shown on the right of FIG. 3, represent the dispensing device 100 when the head 5 has been oriented by a rotation through an angle of 90 degrees clockwise or anticlockwise with respect to the body 3, and with respect to the storage position shown on the left of the same figure.

We can see that, depending on the shape configurations corresponding to the embodiment shown, orienting the head 5 through 45 degrees or 90 degrees with respect to the storage position is likely to present surfaces projecting more widely than the outer surface 7 of the body 3, in certain directions, creating in this case risks of accidentally catching or tearing off the head 5. This demonstrates the interest of including return means for returning the head 5 to the nominal position shown on the left and used to store the dispensing device 100 in a packaging element such as a box or a case adapted to the global shape of the dispensing device 100.

Figure 4:
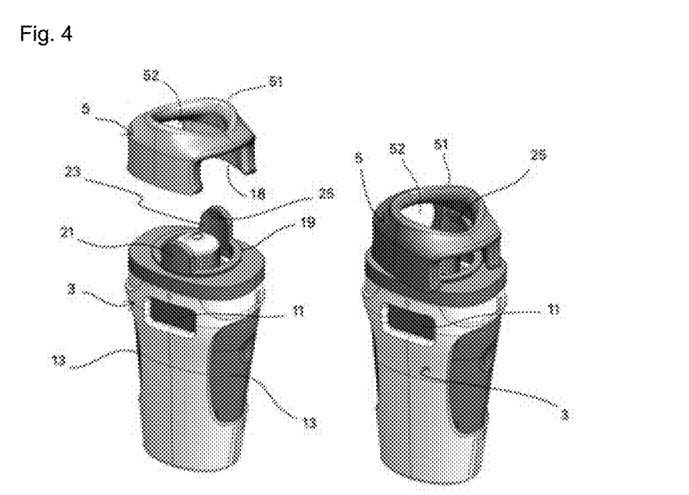
FIG. 4 comprises an exploded perspective view of a dispensing device according to a second embodiment of the invention as well as a view after assembling of the head of the dispensing device on the body and orienting of the head of the dispensing device with respect to the body.

FIG. 4 shows an exploded view (left side of the figure) and a non-exploded view (right side of the figure), in perspective, of the dispensing device 100 according to a second embodiment of the invention.

According to this embodiment of the invention, the connecting means 18, 19 are arranged on a flat or substantially flat surface of the body 3 and the head 5 occupies a greater volume forming a cap adapted to hide and protect the tabs 21 and 23 carrying means for detecting the dispensing of the solution contained in the dispensing device 100.

Advantageously, the dispensing device 100 comprises means for measuring the dispensing and amount of solution dispensed, in order to precisely define the amount of solution dispensed to a patient. This function of the dispensing device 100 is especially useful when dispensing products for which the maximum efficiency corresponds to a dose lying within a predetermined interval of solution volumes.

The display means 11 provide the corresponding information to a user or to a third party who would be monitoring the dispensing of the solution using the dispensing device 100.

According to a preferred embodiment, optoelectronic means are used to detect the solution being dispensed. For example, the body 3 comprises the tabs 21 and 23 partially supporting the connecting means 18, 19 between the body 3 and the head 5 and the tabs 21 and 23 are arranged facing each other and diametrically opposed with respect to the axis of rotation 9 for dispensing the solution. One of the tabs 21, 23 comprises an infrared transmitter 24, not shown on the figure, and the other tab 23, 21 comprises an infrared receiver 25 configured to detect the radiation transmitted by the infrared transmitter arranged opposite. Thus, when dispensing solution, the solution dispensed breaks the infrared beam between the infrared transmitter 24 and the infrared receiver 25 and the amount of solution dispensed can be evaluated depending on the total time during which the beam has been broken during activation by the user of the dispensing device 100. Obviously, this type of configuration requires the use of a control unit adapted to control the optoelectronic elements and visual or audible output elements to provide information concerning the dispensing. This type of control unit traditionally comprises a microcontroller powered by rechargeable or replaceable battery, as well as various elements generally used to implement this type of control unit embedded in a portable dispensing device 100, or an equivalent electronic system. With this type of configuration, all the dispensing measurement means are integrated in the body 3 and there is therefore no need to plan connection means between the body 3 and the head 5.

Figure 5:
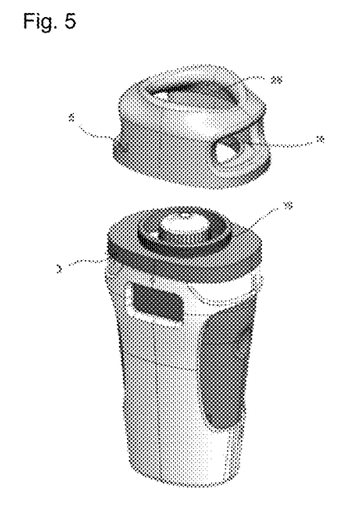
FIG. 5 is an exploded perspective view of a dispensing device according to a third embodiment of the invention.

FIG. 5 shows an exploded perspective view of the dispensing device 100 according to a third embodiment of the invention. According to this embodiment, the shape of the head 5 is similar to that described in the second embodiment described above and illustrated on FIG. 4, but also comprises the optoelectronic means for detecting the solution during a dispensing operation. Thus, there is no longer any need for the tabs 21, 23 arranged on the top flat surface of the dispensing device 100. With this configuration, the connecting means 18, 19, formed by the complementary annular surfaces, comprising respectively at least one rib 19 and one groove 18, comprise conducting elements to make as many electrical connections as necessary to implement the optoelectronic measurement means. The conducting elements are, for example, crowns and rings combined so as to make mechanical and therefore electrical connections between the optoelectronic means and the embedded control unit, including when the head 5 is rotated with respect to the body 3. According to a variant of the embodiment, the flat or substantially flat top surface of the body 3 is equipped with contact shoes made from a conducting material and connected to the control unit, and the head 5 is equipped with crowns also made from a conducting material and connected to the optoelectronic means. According to one embodiment of the invention, four crowns housed in the head 5 are respectively connected to four contact shoes attached to the body 3 to connect the infrared transmitter 24 and the infrared receiver 25 to the control unit embedded in the body 3 of the dispensing device 100.

In other words, and according to one embodiment of the invention, the device 100 for dispensing a solution comprises the body 3, the outer surface 7 of which is intended to be held in at least one of a user's hands, and comprising at least one activation zone 13 that is able to be acted upon by the user to cause the solution to be dispensed. The body 3 of the dispensing device 100 carries the head 5 provided with a contact surface 51 for pressing on an area of the body of a patient. The contact surface 51 of the head 5 forms an outer contour, and comprises at least one orifice, or dispensing opening, for dispensing the solution.

The head 5 is coupled to the body 3 by the connecting means 18, 19 arranged to allow it to rotate with respect to the body 3 in order to modify the position of the contact surface 51 with respect to the activation zones 13 arranged each side of the body 3.

The activation zones 13 have a restricted total surface with respect to the area 7 of the body 3 and are each arranged according to only an angular sector of the outer surface 7 of the body 3, in other words the shape of the activation zones 13 is different from a shape of revolution.

The body 3, the head 5 and the contact surface 51 of the head 5 have a contour whose shape is different from a shape of revolution.

It is understood that the connection carried out by the connecting means 18, 19 can be varied and is preferably chosen from the group: rotation, translation via pivot, ball joint or sliding pivot connection.

The dispensing device 100 may comprise stopper elements adapted to limit the relative rotation of the body 3 of the dispensing device 100 and of its head 5, for example to a maximum angle of 45 degrees or 90 degrees with respect to a nominal position, or storage position, useful when packaging the dispensing device 100.

Optionally, the connecting means 18, 19 may comprise means for returning the head to the storage position.

Artfully, the head 5 is removably mounted with respect to the body 3, thus allowing heads of different shapes to be coupled on the same body 3 of the dispensing device 100.

The invention is not limited to the embodiments described above and other embodiments may be considered. According to a variant, the connection between a control unit embedded in the body and the head carrying optoelectronic detection means may be a wireless connection.

Another embodiment may concern, for example, a dispensing device adapted to the use of thermoformable heads to increase user comfort. According to another example, the dispensing device may be an assistance device for assisting with the dispensing, configured to house a removable and therefore interchangeable tank for the solution. These examples of other embodiments are not limiting.

The invention claimed is:

1. A dispensing device for dispensing a solution, comprising:
    a body having an outer surface configured to be held in at least one of a user's hands, wherein the outer surface comprises at least one activation zone configured to be acted upon by the user to dispense the solution, and
    a head carried by the body, the head comprising a contact surface for pressing on an area of a patient's body, the contact surface forming an outer contour, wherein the head comprises at least one orifice for dispensing the solution, and
    wherein the head is coupled to the body by a connector that allows it to rotate with respect to the body, while being coupled to the body, about an axis of rotation substantially parallel to an axis of the body to modify the position of the contact surface with respect to the at least one activation zone, the dispensing device is configured such that when the contact surface is in contact with the area of the patient's body, the body of the dispensing device is configured to rotate with respect to the head through use of one hand of the user, and
    wherein the dispensing device is configured to dispense the solution in any rotational position of the head with respect to the body.

2. The dispensing device according to claim 1, wherein the at least one activation zone extends over only a portion of the outer surface of the body, and wherein the outer surface of the body further comprises at least one inert zone that cannot be acted upon by the user to dispense the solution.

3. The dispensing device according to claim 2 wherein the outer surface of the body is a peripheral side surface of the body.

4. The dispensing device according to claim 1, wherein the head has a contour having a shape that is different from a shape of revolution.

5. The dispensing device according to claim 1, wherein the body has a contour having a shape that is different from a shape of revolution.

6. The dispensing device according to claim 1, wherein the connection carried out by the connector selected from a pivot connection, a ball joint connection, and a sliding pivot connection.

7. The dispensing device according to claim 1, wherein the connector comprises one or more stopper elements which limit the relative rotation of the body of the dispensing device and the head.

8. The dispensing device according to claim 1, wherein the head is removably mounted with respect to the body.

9. A dispensing device for dispensing a solution, comprising:
    a body having an outer surface configured to be held in at least one of a user's hands, wherein the outer surface comprises at least one activation zone configured to be acted upon by the user to dispense the solution, and
    a head carried by the body, the head comprising a contact surface for pressing on an area of a patient's body, the contact surface forming an outer contour, wherein the head comprises at least one orifice for dispensing the solution, and
    wherein the head and the body are configured to take a relative storage position and wherein the connector comprises a member configured to return the head to its storage position.

10. A dispensing device for dispensing a solution, comprising:
    a body having an outer surface configured to be held in at least one of a user's hands, wherein the outer surface comprises at least one activation zone configured to be acted upon by the user to dispense the solution, wherein the at least one activation zone is separate from an outer wall of a tank containing the solution, and
    a head carried by the body, the head comprising a contact surface for pressing on an area of a patient's body, the contact surface forming an outer contour, wherein the head comprises at least one orifice for dispensing the solution,
    wherein the head is coupled to the body by a connector that allows it to rotate with respect to the body, while being coupled to the body, about an axis of rotation substantially parallel to an axis of the body to modify the position of the contact surface with respect to the at least one activation zone, the dispensing device is configured such that when the contact surface is in contact with the area of the patient's body, the body of the dispensing device is configured to rotate with respect to the head through use of one hand of the user.

11. The dispensing device according to claim 10, wherein the at least one activation zone comprises a mechanical element configured to compress the tank inside the body to dispense the solution contained in the tank.

12. The dispensing device according to claim 10, further comprising an optoelectronic device configured to detect and measure an amount of the solution being dispensed.

13. The dispensing device according to claim 12, wherein the optoelectronic device comprises an infrared transmitter positioned on one side of the connector and an infrared receiver positioned on an opposite side of the connector.

14. The dispensing device according to claim 10, wherein the at least one activation zone extends over only a portion of the outer surface of the body, and wherein the outer surface of the body further comprises at least one inert zone that cannot be acted upon by the user to dispense the solution.

15. The dispensing device according to claim 14 wherein the outer surface of the body is a peripheral side surface of the body.

\* \* \* \* \*